United States Patent [19]
Wenkert

[11] Patent Number: 5,551,284
[45] Date of Patent: Sep. 3, 1996

[54] PORTABLE INSTRUMENT AND METHOD FOR MEASURING THE AIR PERMEABILITY OF PLANT LEAVES

[76] Inventor: William Wenkert, R.D. 1, Box 223-B, Red Hook, N.Y.

[21] Appl. No.: 393,175

[22] Filed: Feb. 23, 1995

[51] Int. Cl.⁶ .......................... G01N 15/08; G01N 33/483
[52] U.S. Cl. .................................................. 73/38; 47/1.01
[58] Field of Search ................................ 73/37, 38, 866; 47/1.01, 48.5

[56] References Cited

U.S. PATENT DOCUMENTS

| | | | |
|---|---|---|---|
| 2,861,451 | 11/1958 | Emmons, III | 73/38 |
| 4,064,740 | 12/1977 | Crosby, Jr. | 73/38 |
| 4,160,374 | 7/1979 | Crump et al. | 73/76 |
| 4,191,046 | 3/1980 | Baker et al. | 73/38 |
| 4,198,853 | 4/1980 | Graham et al. | 73/38 |
| 4,312,218 | 1/1982 | Eckles | 73/866 X |
| 4,401,147 | 8/1983 | Beck et al. | 162/263 |
| 4,854,157 | 8/1989 | Wilson | 73/38 |

OTHER PUBLICATIONS

H. Meidner, Development in Mass Flow Porometry, *Journal of Experimental Botany* 43:1309–1314, 1992.

J. A. Milburn, An Ideal Viscous Flow Porometer, *Journal of Experimental Botany* 30:1021–1034, 1979.

P. E. Weatherly, A Porometer For Use in the Field, *New Phytologist* 65:376–387, 1966.

P. T. Alvin, A New Type of Porometer for Measuring Stomatal Opening and its Use in the Field, *UNESCO And Zone Research* 25:325–329, 1965.

J. F. Bierhuizen et al., A Porometer for Laboratory and Field Operation, *Journal of Experimental Botany*, 30:1021–1034, 1965.

H. Meidner, A Simple Porometer for Measuring the Resistance to Air Flow Offered by the Stomata of Green Leaves *School Sci. Rev* 47:149–151, 1965.

*Primary Examiner*—Michael J. Brock

[57] ABSTRACT

To indicate stomatal aperture in plant leaves, this instrument measures the permeability to air flow across the leaf. Air entrance and exit chambers are temporarily and non-destructively sealed on opposite sides of the leaf. The entrance chamber is pressurized while the exit chamber remains sealed as an initial test for any leakage. The exit chamber is then opened to the atmosphere and the time required for a specific volume of air to move across the leaf is measured.

3 Claims, 1 Drawing Sheet

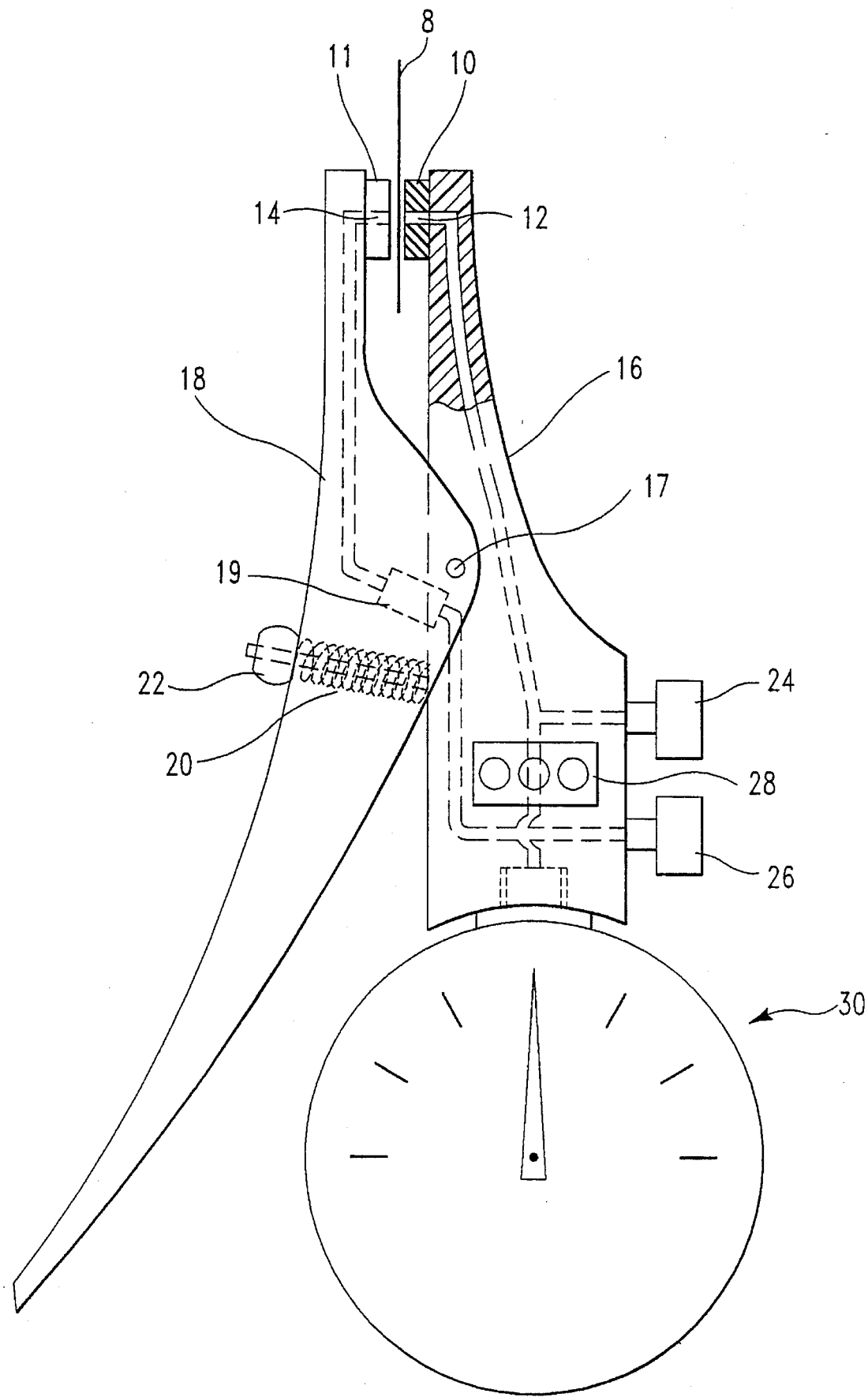

PORTABLE INSTRUMENT AND METHOD FOR MEASURING THE AIR PERMEABILITY OF PLANT LEAVES

BACKGROUND OF THE INVENTION

This invention relates to measuring the permeability to air movement across a plant leaf.

The measurement of permeability to air movement across a leaf has potential importance in plant science because that air moves almost entirely through the adjustable valves, or stomata, on the upper and lower leaf surfaces. Air permeability can thus serve as an indication of how open the stomata are. This is important because only when the stomata are open can the leaf take up carbon dioxide for photosynthesis and lose water in transpiration. Stomata close due to water deficit, low light, disease and other variables, and there has always been a need for a visible indicator of that closure event in plant management, education, and research.

There are three areas of relevant prior art:

a. Various leaf "porometers" which measure air permeability have been developed for plant research purposes (reviewed by Meidner,1981,In Jarvis and Mansfield, *Stomatal Physiology*,Cambridge:Cambridge University Press,pp33–49; and Weyers and Meidner,1990, *Methods in Stomatal Research*,UK:Longman Group). All apply a differential air pressure across the leaf by clamping a sealed chamber on one or both sides and measuring the resulting flow rate. This technique is generally practical only for plants which have stomata on both sides of the leaf, and this is a limitation of the present instrument as well. However, a large majority of plant species, and virtually all crop plants, have stomata on both sides and hence can be measured with this technique.

Most of these experimental air flow porometers have been designed for laboratory work and are completely unsuitable for a portable, rapid, non-destructive measurement in the field. Of those designed for field work (Alvim,1965,A new type of porometer for measuring stomatal opening and its use in irrigation studies,*UNESCO Arid Zone Research*, 25:325–329; Bierhuizen et al.,1965,A poromter for laboratory and field operation,*J.Exp.Bot.*,16:182–191; Weatherly, 1966,A porometer for use in the field,*New Phytol.*, 65:376–387; Milburn,1979,An ideal viscous flow porometer,*J.Exp.Bot.*,30:1021–1034) all suffer from the difficulty of establishing a temporary but absolute seal between the applied pressure chamber and an often rough leaf surface. Without a dependable seal there is no way of knowing how much of the measured flow is actually through the leaf. All these instruments also use a relatively high driving pressure (at least 60 inches of water). This requires potentially damaging clamping pressure and may also influence stomatal aperture in various ways (Meidner, 1981). And none of these instruments is, or is capable of being, self contained in a compact unit held and operated with one hand.

b. Diffusion porometers (such as that commercially available from Li-Cor, Inc., Lincoln, Neb.) have been developed which measure the permeability of the leaf surfaces to water vapor. Since vapor flow, like air flow, is largely through the stomata, this measurement can be related to stomatal opening or "stomatal resistance". All these instruments suffer from errors due to an unknown vapor density within the leaf, small temperature differences between the leaf and air ,and the possibility of influencing stomatal aperture if the instrument stays in contact with the leaf for more than a short time. All these instruments are also bulky and too expensive (more than $6,000 for Li-Cor) to be available to farmers, gardeners, high schools and colleges.

c. Devices for measuring the air permeability of sheet materials have been extensively developed for the paper industry. None of these are obviously adaptable to plant leaves in regard to the requirements of portability, making a non-destructive seal on plant leaf surfaces, or quantifying any lateral leaks which may occur between the gasket and leaf surface.

SUMMARY OF THE INVENTION

Accordingly, one of the purposes of this invention is to satisfy a long-standing need for an affordable, rapid, reliable, portable and non-destructive means to indicate stomatal aperture in plants. It does this by measuring the permeability to air movement across the plant leaf. Measuring leaf permeability to indicate stomatal opening is an old idea, but the present device makes it practical by establishing a temporary but verified seal on the leaf surface and by being conveniently held and operated with one hand.

The invention comprises two air chambers surrounded by flexible rubber gaskets which are clamped on opposite sides of the leaf with an adjustable spring pressure. The air entrance chamber is pressurized to a predetermined value while the exit chamber is closed to the atmosphere. In this state, a constant entrance chamber pressure indicates an air-tight seal between that chamber and the leaf surface. The exit chamber is then opened to the atmosphere and the time required for a predetermined pressure drop to occur is measured. That time interval varies inversely with leaf permeability.

One feature of the present device is that the user is routinely and immediately informed whether an air-tight seal has been established on the leaf surface. This feature is essential for making reliable measurement on new leaves and is not available in any of the prior art.

Another feature of the present device is that all driving pressures are very low (less than 10 inches of water) and this minimizes leaks and leaf distortion which are sources of possible error in prior field instruments.

Another feature of the present device is that it allows the user to select a range of driving pressures (0–10 inches of water). This provides a means of adjusting sensitivity over a range of leaf permeabilities.

Another feature of the present device is that is makes a non-destructive seal on all but very rough or hairy leaf surfaces.

Another feature of the present device is that clamping pressure can be adjusted.

Another feature of the present device is that when there is a small lateral leakage between a rough leaf surface and the entrance chamber gasket, or when there is lateral flow within the leaf tissue (possible in very thick leaves), this can be corrected for. The user can measure this lateral flow while the exit chamber is closed and then subtract that from total flow measured with the exit chamber open. A similar technique was used by Meidner (1992, Developments in mass flow porometry, *J.Exp.Bot.*43: 1309–1314) to measure lateral movement within leaves using a laboratory apparatus, but is not a feature of any prior field instrument.

Another feature of the present device is that is uses dial gauge or electronic gauge instead of a manometer to measure the driving pressure and thus the instrument is rugged and can be used in any orientation.

Another feature of the present device is that the predetermined pressure drop is automatically timed. This simplifies use and avoids user error.

Another feature of the present device is that the measurement normally takes only a few seconds. This ensures that the chamber and air flow haven't influenced the stomata, and it allows many measurements to be made.

Another feature of the present device is that it is entirely self-contained in a unit comfortably held and operated with one hand. This is important for field work and is not available in any of the prior art.

Another feature of the present device is that the simplicity of the theory and components makes it an easy and reliable instrument for laymen's use. This is not true of any of the prior art.

Another feature of the present device is that its simplicity of theory and components allows it to be produced inexpensively enough to become available to a wide range of laymen, plant managers, and educators who have no affordable options for such a measurement now.

Further features will become more apparent in the following description.

BRIEF DESCRIPTION OF THE DRAWING

FIG. 1 shows the preferred embodiment of the instrument.

DESCRIPTION OF THE PREFERRED EMBODIMENT

A typical embodiment of the instrument is illustrated in FIG. 1. Soft gaskets 10 and 11 made from silicone (RTV 12 two-part silicone, manufactured by General Electric Co., Waterford, N.Y.) have openings which form entrance and exit chambers 12 and 14 on opposite sides of the leaf 8. The gaskets 10 and 11 each have an adhesive side which adheres them to the clamp body 16 and the clamp arm 18. The clamp arm 18 is hinged on a pin 17. A clamp spring 20 forces the gaskets closed on the leaf 8, and this clamping pressure is adjusted by a clamp adjusting nut 22.

The entrance chamber 12 communicates via a port 12A in the clamp body 16 with a finger pump 24 and a pressure gauge 30. The exit chamber 14 communicates via a port 14A in the clamp arm 18 with a flexible coupling 19 and then a port in the clamp body 16 which leads to the exit chamber release valve 26. Pushing the valve 26 both opens the exit chamber 14 to the atmosphere and starts the stopwatch 28 which stops when the valve is released.

To operate, the user swings open the clamp arm 18 with the same hand which holds the instrument. The leaf is slid between the silicone gaskets 10 and 11 and the clamp arm is then released. The exit and entrance chambers 12 and 14 are now sealed on opposite sides of the leaf. The user then presses the finger pump 24 until some predetermined initial driving pressure (determined by experience) is established in the gauge 30 and the entrance chamber 12. If the pressure remains constant for a few seconds, then this indicates that a sufficiently air-tight seal has been established on the entrance chamber 12 side of the leaf.

The user then opens the exit chamber 14 by pressing the release valve 26. This starts the electronic stopwatch If the leaf has stomata on both sides, and if the stomata are sufficiently open, then air will be forced across the leaf and the pressure on the gauge will be seen to fall. When the predetermined final driving pressure (determined by experience) is reached, the user stops depressing the exit chamber release valve 26 and this stops both the air flow and the stopwatch 28. The measured pressure drop corresponds to a specific air volume which has travelled through the leaf, and the time required for this is inversely proportional to leaf permeability.

For comparisons between instruments which differ in chamber area, driving pressure, or the internal volume of the instrument, a permeability P can be defined by $$P = V/t \times \Delta p \times A$$

where V is the air volume which travels through the leaf over the measured time period t, $\Delta p$ is the mean pressure difference across the leaf, i.e. the midpoint of the initial and final driving pressures, and A is the area of leaf exposed in the entrance chamber.

When measuring leaves which are rough or hairy there may be a lateral leak from the entrance chamber 12 between the silicone gasket 10 and leaf chamber 8. This will be indicated in the initial stage of the measurement by a falling pressure in the gauge 30 after the entrance chamber 12 has been pressurized and while the exit chamber 14 is still closed. The user can then increase the clamping pressure by moving the clamp adjusting nut 22 until the entrance chamber pressure remains constant.

For some leaves the initial entrance chamber pressure cannot be stabilized—either because higher clamping pressure is ineffective or judged to be damaging to the leaf, or because air is moving into the leaf and then laterally through the leaf tissue. In this case the user of the present invention has the option of still being able to estimate permeability across the leaf as follows: The lateral flow is measured by timing the pressure drop while the exit chamber remains closed; then the entrance chamber is pressurized again and the total flow measured with the exit chamber open. The first is subtracted from the second to yield through-flow.

The user can adjust the sensitivity of the instrument to match a wide range of leaf permeabilities in several ways:

(a) By choosing a higher or lower driving pressure.

(b) By varying leaf area measured. This is accomplished by substituting different silicone gaskets 10 and 11 which have a larger or smaller entrance and exit chamber 12 and 14.

(c) By changing the instrument's capacitance, or the correspondence between change in its internal volume and change in pressure. Sensitivity could be decreased in the present embodiment shown in FIG. 1 by connecting various air reservoirs in parallel with the dial pressure gauge 30. Sensitivity could be increased by using an embodiment which has an electronic pressure gauge instead of the dial gauge. This would require a much smaller change in volume to register a specific change in pressure.

The above should not be construed as limiting the scope of the invention but as merely providing illustrations of some of the presently preferred embodiments.

What is claimed is:

1. A instrument held in one hand for measuring the air permeability of a plant leaf comprising:

air inlet means which is placed over at least a part of a leaf surface and air outlet means which is placed over at least a part of the opposite surface;

means for holding the air inlet and air outlet means in place on the surfaces of the leaf while measurements of the air permeability between the air inlet and the air outlet are taken;

pump means for introducing pressurized air in order to pressurize the air inlet;

means for measuring the pressure of air at the air inlet;

means for releasing the pressurized air from the air outlet;

means for timing any change in air inlet pressure while the air outlet means remains closed; and means for timing any change in air inlet pressure after the air outlet means is opened.

2. An instrument held in one hand for measuring the air permeability of a leaf comprising:

entrance and exit chambers surrounded by flexible but firm gaskets;

a clamp affixed to said chambers, which can be opened with the same hand which holds the instrument and with that some hand closed on opposite sides of the leaf;

a spring attached to said clamp which provides a steady, but adjustable, clamping pressure throughout a measurement;

a finger pump, which pressurizes the entrance chamber, which is operated by the same hand which holds the instrument;

a dial pressure gauge which measures the entrance chamber pressure;

an exit chamber release valve which is operated by the same hand which holds the instrument; and a timing device which in routine use starts when the exit chamber release valve is pressed and stops when the valve is released.

3. An instrument as in claim 2 wherein the pressure gauge is electronic.

* * * * *